(12) United States Patent
Park et al.

(10) Patent No.: US 10,898,229 B2
(45) Date of Patent: Jan. 26, 2021

(54) EXTERNAL FIXATOR HAVING ROTATABLE BONE REDUCTION FRAME

(71) Applicant: Kyungpook National University Industry-Academic Cooperation Foundation, Daegu (KR)

(72) Inventors: Ilhyung Park, Gyeongsangbuk do (KR); Changwug Oh, Daegu (KR); Hyunwoo Lee, Daegu (KR); Sanghyun Joung, Daegu (KR); Chulwoo Park, Daegu (KR)

(73) Assignee: Kyungpook National University Industry-Academic Cooperation Foundation, Daegu (KR)

( * ) Notice: Subject to any disclaimer, the term of this patent is extended or adjusted under 35 U.S.C. 154(b) by 253 days.

(21) Appl. No.: 15/998,569

(22) PCT Filed: Sep. 1, 2016

(86) PCT No.: PCT/KR2016/009764
§ 371 (c)(1),
(2) Date: Aug. 15, 2018

(87) PCT Pub. No.: WO2017/142148
PCT Pub. Date: Aug. 24, 2017

(65) Prior Publication Data
US 2020/0275953 A1 Sep. 3, 2020

(30) Foreign Application Priority Data

Feb. 15, 2016 (KR) ........................ 10-2016-0016996

(51) Int. Cl.
*A61B 17/66* (2006.01)

(52) U.S. Cl.
CPC .................................. *A61B 17/66* (2013.01)

(58) Field of Classification Search
CPC ......... A61B 17/88; A61B 17/60; A61B 17/62; A61B 17/66; A61B 17/6416;
(Continued)

(56) References Cited

U.S. PATENT DOCUMENTS 5,971,984 A * 10/1999 Taylor .................... A61B 17/62
 128/898
8,202,273 B2 * 6/2012 Karidis .................. A61B 17/62
 606/56

(Continued)

FOREIGN PATENT DOCUMENTS

KR 10-2004-0037221 A 5/2004
KR 10-2004-00377221 * 5/2004 ............. A61B 17/66
(Continued)

*Primary Examiner* — Pedro Philogene
(74) *Attorney, Agent, or Firm* — Novick, Kim & Lee, PLLC; Sang Ho Lee

(57) ABSTRACT

Provided is an external fixator having a rotatable bone reduction frame for reduction of a fractured or deformed bone, which includes: a first frame through which the bone passes; a second frame through which the bone passes, the second frame being spaced apart from the first frame; a variable leg having both ends respectively connected to the first frame and the second frame and having a changeable length; and a rotating frame mounted to at least one frame of the first frame and the second frame to surround the bone entirely or partially, the rotating frame being rotatable based on at least one direction of a horizontal direction traversing the at least one frame and a vertical direction perpendicular to the horizontal direction as an axial direction.

18 Claims, 14 Drawing Sheets

(58) Field of Classification Search
CPC ........... A61B 2017/00734; A61B 2017/00398; A61B 2017/564; A61B 2017/606; A61B 2017/00725; A61B 900/37; A61B 93/0639; A61B 2090/061; A61B 2090/063; A61B 2090/0807; A61B 2090/031; A61B 2090/0812; A61B 2090/064; A61B 2090/067; A61B 34/10; A61B 34/25; A61B 2034/252; A61B 2034/105; A61B 2034/108; G06F 3/04847; G16H 20/40; G16H 30/40; G16H 40/63
USPC ...................................................... 606/56–59
See application file for complete search history.

(56) References Cited

U.S. PATENT DOCUMENTS

| | | | |
|---|---|---|---|
| 9,788,861 B2* | 10/2017 | Murray | A61B 17/62 |
| 9,895,167 B2* | 2/2018 | Edelhauser | A61B 17/62 |
| 10,082,384 B1* | 9/2018 | Singh | A61B 17/62 |
| 2011/0004199 A1 | 1/2011 | Ross et al. | |
| 2015/0272624 A1* | 10/2015 | Singh | A61B 17/62 606/56 |

FOREIGN PATENT DOCUMENTS

| | | | | |
|---|---|---|---|---|
| KR | 10-0595479 B1 | | 7/2006 | |
| KR | 10-1501635 | * | 3/2015 | ............ A61B 17/66 |
| KR | 10-1501635 B1 | | 3/2015 | |
| KR | 10-1576798 B1 | | 12/2015 | |

* cited by examiner

EXTERNAL FIXATOR HAVING ROTATABLE BONE REDUCTION FRAME

TECHNICAL FIELD

The present disclosure relates to an external fixator having a rotatable bone reduction frame, and more particularly, to an external fixator having a rotatable bone reduction frame, which forms a broad bone reduction area and has the rotation degree of freedom.

BACKGROUND ART

Minimally invasive fracture reposition surgery is a fracture reposition surgery that minimizes the incision of the patient. In the fracture reposition surgery, a real-time X-ray equipment such as a C-ARM is used for reduction of the displaced bone, in which, an intramedullary nail is inserted in the repositioned state to fix the corrected bone fragments.

An external fixator used in the fracture reposition surgery includes upper and lower frames, a variable leg for connecting the upper frame and the lower frame and changing the length thereof to change the relative positions of the upper frame and the lower frame and applying a force for reduction to the bone, and a fixing member for fixing a bone fragment of the fractured or deformed bone. Additionally, a frame may be provided on upper and lower frames.

In this regard, a conventional external fixator (Korean Patent No. 10-0595479) discloses that a frame installed additionally on upper and lower frames is used in a fixed state without rotating based on a horizontal direction or a vertical fixed direction as an axial direction. Thus, it is difficult to expand the bone reduction area and the rotational degree of freedom of the frame is not ensured. Thus, the bone condition that can be effectively corrected is limited.

DISCLOSURE

Technical Problem

In order to solve the above problems, it is necessary to invent an external fixator, which additionally includes a rotatable frame to have a broad bone reduction area and is also capable of inducing free alignment by ensuring the rotation degree of freedom.

The present disclosure is directed to provide an external fixator, which additionally includes a rotating frame on upper and lower frames, which is rotatable based on at least one of a horizontal direction and a vertical direction as an axial direction, to have a substantially broad bone reduction area and also allows bone reduction for various kinds of bone damages.

The objects to be solved by the present disclosure are not limited to the above, and other objects not mentioned herein can be clearly understood from the following disclosure by those skilled in the art.

Technical Solution

In one general aspect, there is an external fixator provided, having a rotatable bone reduction frame for reduction of a fractured or deformed bone, comprising: a first frame through which the bone passes; a second frame through which the bone passes, and the second frame being spaced apart from the first frame; a variable leg having both ends respectively connected to the first frame and the second frame and having a changeable length; and a rotating frame mounted to at least one frame of the first frame and the second frame to surround the bone entirely or partially, the rotating frame being rotatable based on at least one direction of a horizontal direction traversing the at least one frame and a vertical direction perpendicular to the horizontal direction as an axial direction.

Advantageous Effects

According to the present disclosure, it is possible to provide an external fixator, which may additionally include a rotatable frame to have a broad bone reduction area and also be capable of inducing free alignment by ensuring the rotation degree of freedom.

Figure 1:
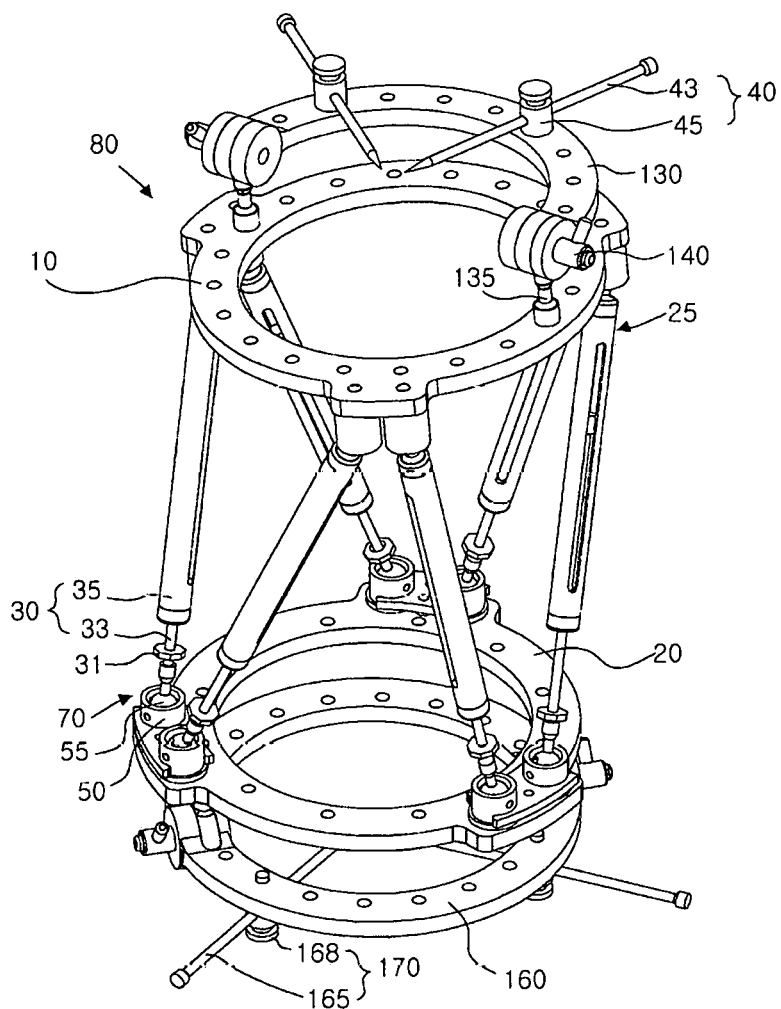
FIG. 1 is a perspective view showing an external fixator having a rotatable bone reduction frame according to an embodiment of the present disclosure.

| [Reference Signs] | |
|---|---|
| 10: first frame | 20: second frame |
| 25: spherical joint | 30: variable leg |
| 31: shaft fixing device | 33: first leg |
| 35: second leg | 40, 170: fixing member |
| 43, 165: pin | 45: fixture |
| 50: ball housing | 53: fitting groove |
| 55: ball | 57: ball axle |
| 59: insert hole | 60: perforation hole |
| 63: pin member | 65: lower space |
| 70: ball joint | 80, 220, 230: external fixator |
| 90: surgical actuator | 91: motor frame |
| 93, 105: motor | 95, 107: motor drive |
| 97, 110: driving unit | 100: portable actuator |
| 130, 160, 190, 210: frame body | 135, 175: support member |
| 140, 180, 200: horizontal fixing lever | 240: guide frame |

-continued

[Reference Signs]

245: rotating body
260: roller
267, 269: stop pin
275: vertical fixing lever

250: opening frame
265: mounting pin
270: cover

BEST MODE

The advantages and features of the present disclosure and the method for accomplishing the same will be apparent from the following description with reference to the accompanying drawings. However, the present disclosure is not limited to the embodiments described herein but can be implemented in various ways. The embodiments are just to make the present disclosure to be completely understood by those skilled in the art, and the present disclosure is defined only by the scope of the claims. Throughout the drawings, like reference signs refer to like components.

The terminology used herein is for the purpose of describing particular embodiments only and is not intended to be limiting of the present disclosure. In the specification, the singular forms are intended to include the plural forms as well, unless the context clearly indicates otherwise. It will be further understood that the terms "comprises" and/or "comprising" used in this specification do not preclude the presence or addition of one or more other elements, steps and operations.

Figure 2:
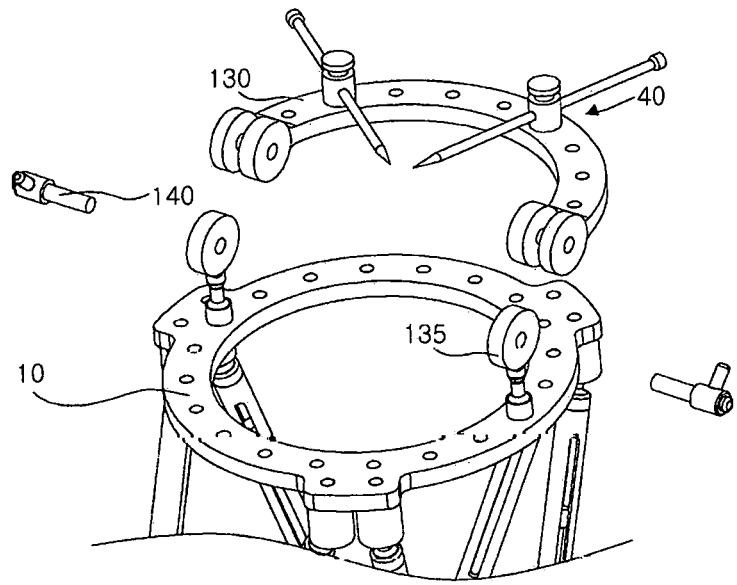
FIGS. 2 and 3 are exploded views showing the rotatable bone reduction frame according to an embodiment of the present disclosure.
Figure 3:
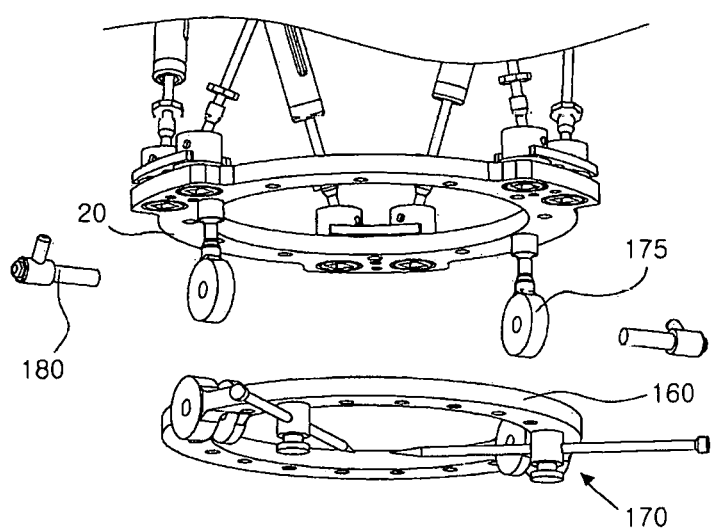

An external fixator having a rotatable bone reduction frame according to an embodiment of the present disclosure will be described with reference to FIGS. 1 to 5C. FIG. 1 is a perspective view showing an external fixator having a rotatable bone reduction frame according to an embodiment of the present disclosure. FIGS. 2 and 3 are exploded views showing the rotatable bone reduction frame according to an embodiment of the present disclosure. FIGS. 4A to 5C are diagrams for illustrating a rotating process of the rotatable bone reduction frame according to an embodiment of the present disclosure.

Referring to FIGS. 1 to 5C, an external fixator 80 having a rotatable bone reduction frame according to an embodiment of the present disclosure is an external fixator for reduction of the fractured or deformed bone and includes a first frame 10, a second frame 20, a variable leg 30 and a rotating frame.

The first frame 10 and the second frame 20 constitute both end portions and upper and lower portions of the external fixator 80, respectively. In some cases, the first frame 10 may be regarded as an upper frame and the second frame 20 may be regarded as a lower frame. The first frame 10 and the second frame 20 have a perforation therein so that the bone of the arm or leg of a patient may pass through the inside of the first frame 10 and the second frame 20. Since the first frame 10 and the second frame 20 have a perforation as above, the external fixator 80 may surround a fractured or deformed part of the bone. The perforation may have various shapes, such as circular and polygonal shapes, and there is no limit to the shape as long as it is possible to surround the arm or leg of the patient.

Meanwhile, at least one of the first frame 10 and the second frame 20 may be composed of a plurality of sub frames, and the sub frames may be connected using a coupling component as a bolt and a nut. If the first frame 10 or the second frame 20 is composed of a plurality of sub frames, it is not needed to mount an external fixing device from an end of the leg or arm of a patient so that the external fixator 80 surrounds the fractured or deformed part of the bone. Instead, after releasing the coupling between the sub frames and opening the released sub frames, the external fixator 80 may be immediately attached to the fractured or deformed part of the bone.

The variable leg 30 is a member connecting the first frame 10 and the second frame 20 since one end thereof is connected to the first frame 10 and the other end thereof is connected to the second frame 20. In addition, the variable leg 30 may change its length to change the relative positions and postures of the first frame 10 and the second frame 20. In this regard, the process of changing the length of variable leg 30 will be described. First, the variable leg 30 may include a first leg 33 and a second leg 35, and an actuator such as a motor is provided inside the variable leg 30, so that the first leg 33 and the second leg 35 move relative to each other by the actuator, thereby changing the length of the variable leg 30. Alternatively, there is no actuator provided in the variable leg 30 and a detachable actuator may be separately applied, which is separated from the external fixator.

Also, the variable leg 30 may be connected to the first frame 10 and the second frame 20 through a joint structure such as a spherical joint 25 or a ball joint 70, and as a result, the angle formed between the first and second frames 10, 20 and the variable leg 30 may be changed. Since the length of the variable leg 30 is changed and also the spherical joint 25 or the ball joint 70 is used, the external fixator 80 may perform effectively the external fixation to the bones fractured or deformed in various forms. However, the coupling method between the variable leg 30 and the first and second frames is not limited to the above, and any coupling method may be applied without limitation as long as the external fixation may be effectively performed.

Meanwhile, the number of variable legs 30 may be six, but the number of variable legs 30 may vary depending on the type and purpose of surgical operation.

The rotating frame may be installed at the first frame 10 and the second frame 20 or may be detachably mounted thereto to form a space therein, which may surround the bone entirely or partially. Accordingly, the external fixator 80 has a broad bone reduction area. Also, since the rotating frame is rotatable based on a horizontal direction traversing the first frame 10 or the second frame 20 as an axial direction, the rotating frame may add the rotation degree of freedom to the external fixator, thereby allowing external fixation of a fractured or deformed bone more efficiently.

The rotating frame may include a first rotating frame installed on the first frame 10 and a second rotating frame installed on a bottom of the second frame 20, which is not directly connected to the variable leg 30. The first rotating frame may include a frame body 130 with a semicircular shape, a support member 135 for supporting the frame body 130 onto the first frame 10, and a horizontal fixing lever 140 for blocking rotation of the frame body 130.

In detail, insert spaces are formed at both ends of the frame body 130 with a semicircular shape, and perforation holes are formed at both sides defining the insert space to be located on the same line. The support member 135 is inserted into the insert space of the frame body 130 so that the perforation hole of the support member 135 and the perforation holes at both sides of the frame body 130 are positioned on the same line, and the horizontal fixing lever 140 is inserted into the perforation holes so that the frame body 130 is rotatably fastened to the support member 135.

In addition, the support member 135 coupled to the frame body 130 may be fixedly or detachably mounted on the first frame 10, and by this coupling, the first rotating frame may be mounted on the first frame 10.

Meanwhile, since the frame body 130 has a semicircular shape, an open portion exists, and a hip portion may be surrounded by the open portion. Thus, the external fixator 80 according to an embodiment of the present disclosure is effective for reduction treatment of a fractured bone on a body part that the external fixator is not able to cover entirely.

Figure 4A:
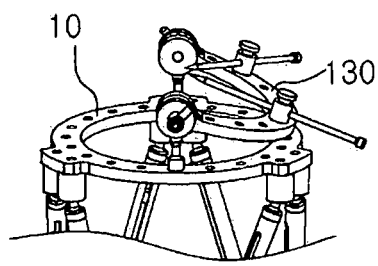
FIGS. 4A to 5C are diagrams for illustrating a rotating process of the rotatable bone reduction frame according to an embodiment of the present disclosure.
Figure 4B:
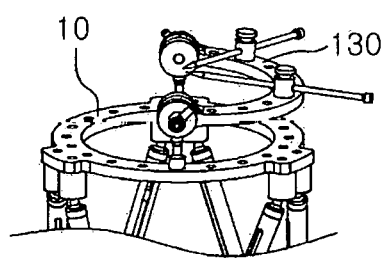
Figure 4C:
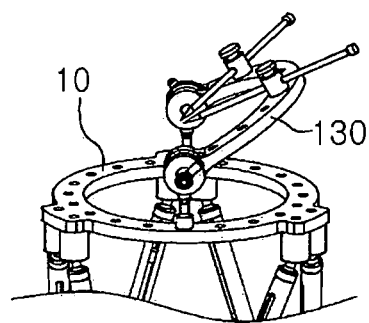
Figure 5A:
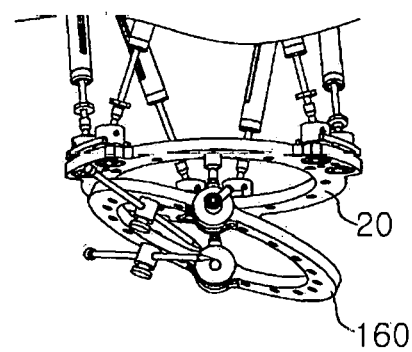
Figure 5B:
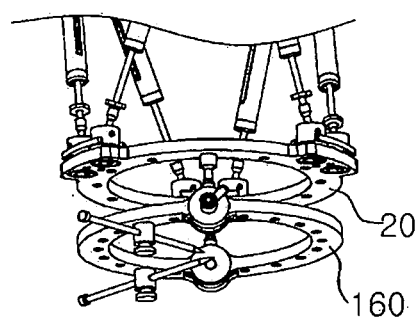
Figure 5C:
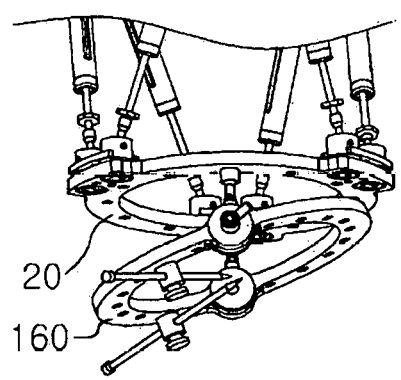

Seeing the rotating process of the first rotating frame with reference to FIGS. 4A to 4C, in a state where the horizontal fixing lever 140 is released, the frame body 130 of the first rotating frame may be inclined to the right on the figure (see FIG. 4A), and after that, the frame body 130 may be lifted upward to come to a horizontal state (see FIG. 4B), and the frame body 130 may be further lifted to be tilted from an upper right side to a lower left side (see FIG. 4C). In other words, the frame body 130 is rotatable based on a virtual axis in the horizontal direction connecting the perforation holes at both sides of the frame body 130.

If the frame body 130 is positioned as desired by a medical worker or patient through this rotating process, the position of the frame body 130 is fixed by means of the horizontal fixing lever 140 to block the rotation thereof. In relation to the blocking of the rotation of the frame body 130, since the horizontal fixing lever 140 includes a front length portion having a cylindrical shape and a small diameter and a rear length portion having a cylindrical shape and a larger diameter than the front length portion, a protrusion is formed at a region changing from the front length portion to the rear length portion to form a step (See FIG. 2). Also, as the protruding horizontal fixing lever 140 applies a pressure to the side portion forming an insert portion of the frame body 130, the side portion is pressed to the support member 135 to fit into the insert portion, and as a result, it prevents the first rotating frame from rotating. However, the front length portion and the rear length portion may have various shapes such as a prismatic shape other than a cylindrical shape.

Since the first rotating frame is installed on the first frame 10, the external fixator 80 is extended in the vertical direction as a whole. Also, as the external fixator 80 rotates based on the horizontal direction as an axis without being maintained in a horizontal state, the external fixator 80 has a wide bone reduction area and an increased rotation degree of freedom, thereby ensuring effective reduction of the bond damaged in various ways.

Moreover, a fixing member 40 for anchoring a bone fragment to the first rotating frame is installed at the frame body 130 of the first rotating frame. The fixing member 40 is a member for anchoring the bone fragment of the fractured or deformed bone to the first rotating frame. To anchor the bone fragment, the fixing member 40 may include a pin 43 stuck into the bone fragment and a fixture 45 for fixing the pin 43 onto the first rotating frame.

In addition, a second rotating frame is installed at a bottom of the second frame 20. The seconds rotating frame includes a frame body 160, a support member 175, a horizontal fixing lever 180 and a fixing member 170, similar to the first rotating frame. However, unlike the first rotating frame, the frame body 160 has a circular shape. Meanwhile, the rotating and fixing principle of the second rotating frame is the same as the first rotating frame. As seen from FIGS. 5A to 5C, the frame body 160 may be in an inclined state to the left on the figure (see FIG. 5A), in a horizontal state (see FIG. 5B) or an inclined state to the right (see FIG. 5C). In other words, the second rotating frame is rotatable around a virtual axis connecting the perforation holes at both sides of the frame body 160.

Meanwhile, the rotating frame may be composed of a plurality of sub frames, and the sub frames may be connected using a coupling component such as a bolt and a nut. If the rotating frame is composed of a multiple plurality of sub frames, it is not needed to mount the rotating frame from one end of the leg or arm of the patient so that the rotating frame surrounds the fractured or deformed part of the bone. Instead, after releasing the coupling between the sub frames and opening the released sub frames, the rotating frame may be immediately attached to the fractured or deformed part of the bone.

Figure 6:
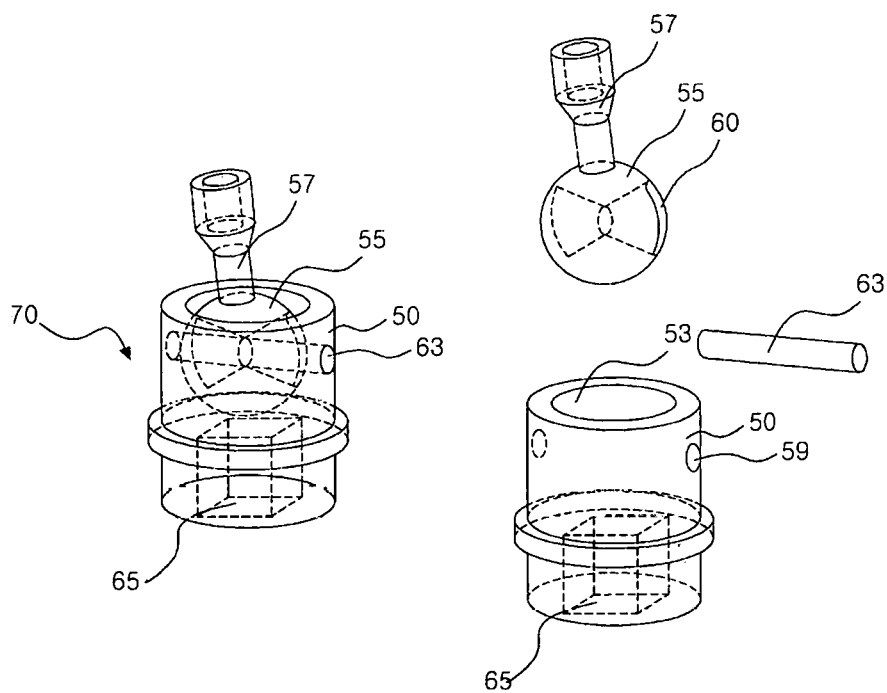
FIG. 6 is an exploded view showing a ball joint of the external fixator having a rotatable bone reduction frame according to the present disclosure.
Figure 7:
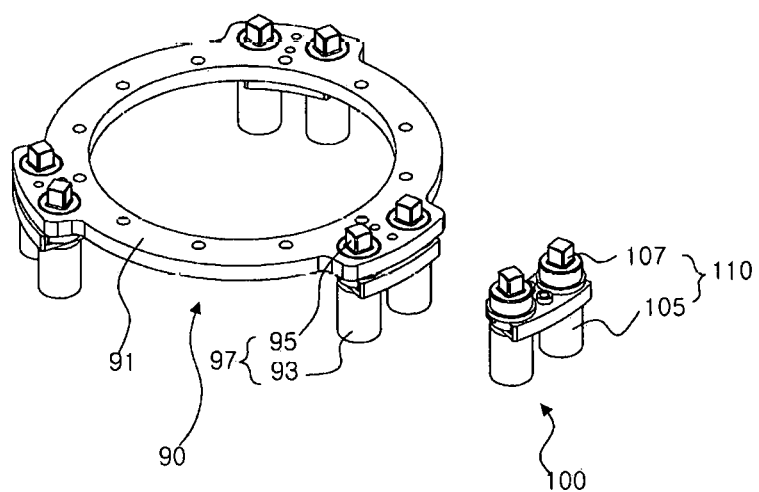
FIG. 7 is a diagram showing an actuator of the external fixator having a rotatable bone reduction frame according to the present disclosure.

In addition, a ball joint structure and an actuator applicable to the external fixator 80 having a rotatable bone reduction frame according to an embodiment of the present disclosure will be described with reference to FIGS. 6 and 7. FIG. 6 is an exploded view showing a ball joint of the external fixator having a rotatable bone reduction frame according to the present disclosure. FIG. 7 is a diagram showing an actuator of the external fixator having a rotatable bone reduction frame according to the present disclosure.

As described above, the variable leg 30 of the external fixator 80 having a rotatable bone reduction frame according to an embodiment of the present disclosure may change its length by means of a separate detachable actuator. For this, the shape of the variable leg 30 and the structure of the ball joint 70, explained later, may be applied to connect the variable leg 30 and the second frame 20.

The variable leg 30 includes a first leg 33 with a male thread and a second leg 35 with a female thread to make screw coupling with the male thread. The entire length of the variable leg 30 may vary by fastening or releasing the screw coupling between the male thread and the female thread, and as a result, the relative positions and postures of the first frame 10 and the second frame 20 may be changed.

The ball joint 70 is a member for connecting the variable leg 30 and the second frame 20 serving as a lower frame and may include a ball axle 57 connected to the first leg 33 of the variable leg 30, a ball 55 formed at the other end of the ball axle 57, a ball housing 50 installed at the second frame 20 and having a fitting groove 53 into which the ball 55 is fit, and a pin member 63.

In addition, the ball 55 has a perforation hole 60 passing through the center of the ball 55. Also, a pair of insert holes 59 is formed at an outer surface of the ball housing 50 to face each other along a direction traversing the fitting groove 53. As the rod shape pin member 63 passes through one insert hole 59 of the ball housing 50, passes through the perforation hole 60 of the ball 55, and then passes through the other insert hole 59 of the ball housing 50, the pin member 63 may extend over the pair of insert holes 59 and simultaneously pass through the perforation hole 60 of the ball 55.

Moreover, the perforation hole 60 of the ball 55 may have the same diameter as the pin member 63 at the center thereof, and thus the pin member 63 may engage with the perforation hole 60 at the center of the ball 55. Meanwhile, a portion of the perforation hole 60 on the spherical surface of the ball 55 may have a slit shape, and the area of the slit shape is larger than a sectional area of the pin member 63, thereby ensuring the pivot movement of the ball 55.

In addition, a lower space 65 is formed in the lower part of the ball housing 50, and a protrusion of the actuator, explained later, is inserted into the lower space 65. Thus, the rotation force of the actuator is transmitted to the ball housing 50 to rotate the ball housing 50.

The ball housing 50 is installed on the second frame 20. For the installation, in the present disclosure, two ball housings 50 adjacent to each other form one group, and three groups in total may be installed at a predetermined interval on the second frame 20. However, the installation method of the ball housing 50 may be performed in various ways and is not limited to the above.

The actuator is a driving device that changes the length of the variable leg 30 of the external fixator 80 and may include a surgical actuator 90 and a portable actuator 100. The surgical actuator 90 may include a driving unit 97 with a motor 93 and a motor frame 91 to which the driving unit 97 is mounted. In addition, the driving unit 97 may include a motor 93 with an encoder attached thereto and a motor drive 95 connected to the motor 93 and serving as a power transmission member rotated by the power of the motor 93. Also, a protrusion is formed at the upper portion of the motor drive 95.

Meanwhile, the protrusion of the motor drive 95 is fit into the lower space 65 of the ball housing 50 so that the ball housing 50 and the motor drive 95 move integrally. In this structure, the motor drive 95 is rotated by the motor 93, and as a result, the ball housing 50 coupled to the motor drive 95 also rotates. In addition, the ball 55 connected to the first leg 33 is present in the ball housing 50 and united to the ball housing 50 by the pin member 63. Thus, if the ball housing 50 is rotated by the driving unit 97, the first leg 33 connected to the ball 55 is rotated, and as a result, the first leg 33 moves into the second leg 35 along the rotation direction, thereby shortening the length of the variable leg 30, or the first leg 33 moves out of the second leg 35, thereby elongating the length of the variable leg 30.

Moreover, two driving unit 97, each including the motor 93 and the motor drive 95, may be bound by a mounting bracket to form one power group. Also, three power groups are installed on the motor frame 91, and on the motor frame 91, one power group is installed at a location corresponding to the ball housing 50 mounted to the second frame 20. Thus, when the surgical actuator 90 is mounted to the external fixator 80, the motor drive 95 of the surgical actuator 90 may be accurately fit into the lower space 65 of the ball housing 50.

The portable actuator 100 is a driving member used when a medical worker or a patient performs progressive bone reduction after surgical operation and may be composed of two driving units 110, each having a motor 105 and a motor drive 107. Two driving units 110 may be bound together to a mounting bracket to form one power group, which serves as the portable actuator 100.

Meanwhile, the operating times and operation details of the surgical and portable actuators described above may be adjusted by a server, which may enhance the bone reduction effect. Also, the operation details may include the rotational force of the motor, the rotating direction, and the like.

In addition, a shaft fixing device 31 with a nut shape may be installed at the first leg 33 with a male thread. The shaft fixing device 31 may be moved up or down on the first leg 33 by fastening or releasing the screw coupling. Accordingly, on the first leg 33, the shaft fixing device 31 may be moved up to a position contacting the lower end of the second leg 35 to prevent the second leg 35 from moving downward, so that the axis of the variable leg 30 may be fixed without changing the length.

Figure 8:
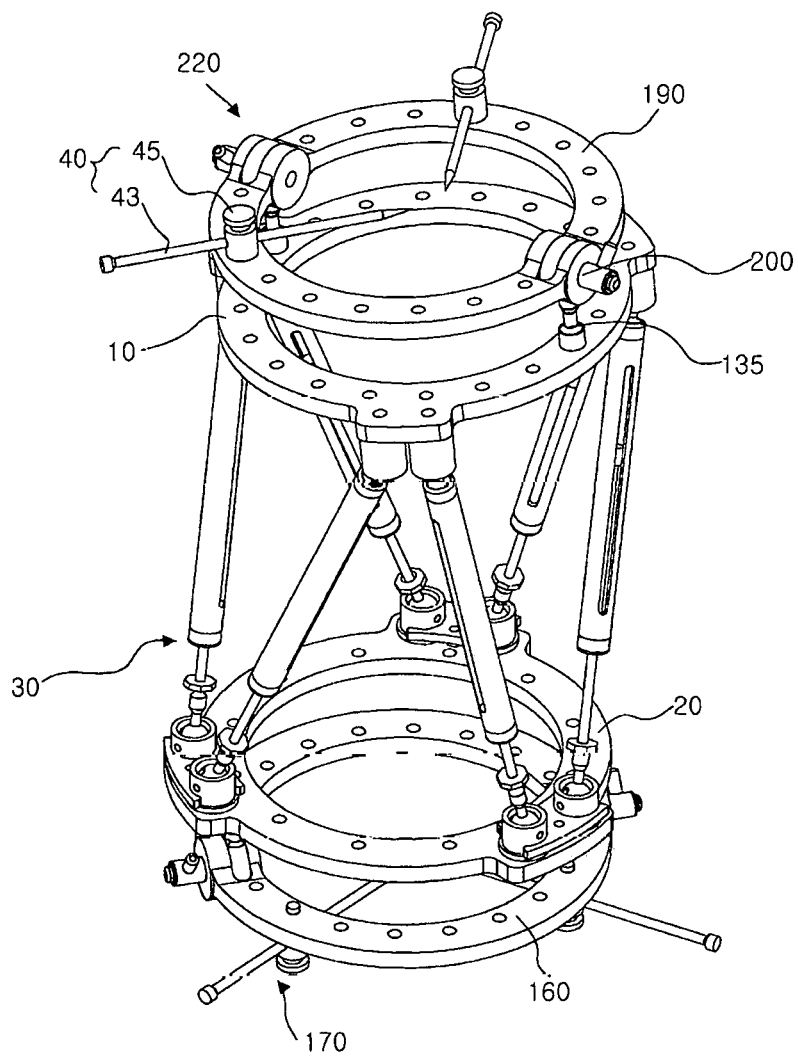
FIG. 8 is a perspective view showing an external fixator having a rotatable bone reduction frame according to another embodiment of the present disclosure.

The external fixator 80 having a rotatable bone reduction frame according to one of the embodiments of the present disclosure has been described. Hereinafter, an external fixator having a rotatable bone reduction frame according to another embodiment of the present disclosure will be described with reference to FIG. 8. FIG. 8 is a perspective view showing an external fixator having a rotatable bone reduction frame according to another embodiment of the present disclosure.

Referring to FIG. 8, in an external fixator 220 having a rotatable bone reduction frame according to another embodiment of the present disclosure, a frame body 190 of the rotating frame installed on the first frame 10 has a circular shape, instead of a semicircular shape, and the frame body 190 may be rotated or blocked from rotating by releasing or fastening the horizontal fixing lever 200, similar to the external fixator 80 according to the former embodiment of the present disclosure. In addition, since the frame body 190 has a circular shape, the installation range of the fixing member 40 is widened. As a result, when the bone fragment is anchored, the degree of freedom in adjusting the distance between the fixing members 40 may increase, thereby effectively anchoring the bone fragment.

Figure 9:
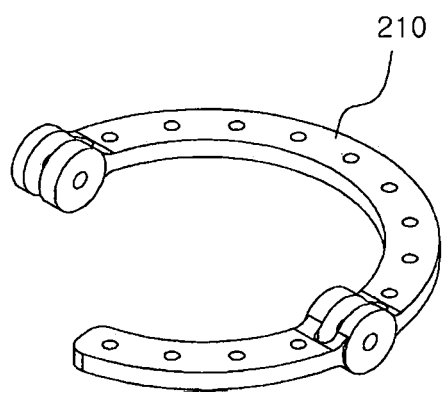
FIG. 9 is a diagram showing a rotatable bone reduction frame according to still another embodiment of the present disclosure.

The external fixator 220 having a rotatable bone reduction frame according to another embodiment of the present disclosure has been described. Hereinafter, an external fixator having a rotatable bone reduction frame according to yet another embodiment of the present disclosure will be described with reference to FIG. 9. FIG. 9 is a diagram showing a rotatable bone reduction frame according to yet another embodiment of the present disclosure.

Referring to FIG. 9, in an external fixator having a rotatable bone reduction frame according to yet another disclosure of the present disclosure, a frame body 210 of the rotating frame may have a fan shape between a circular shape and a semicircular shape. Since the shape of the frame body 210 may be adjusted to a fan shape between a circular shape and a semicircular shape, the external fixator may be effectively applied to various fractured parts of the body.

Figure 10:
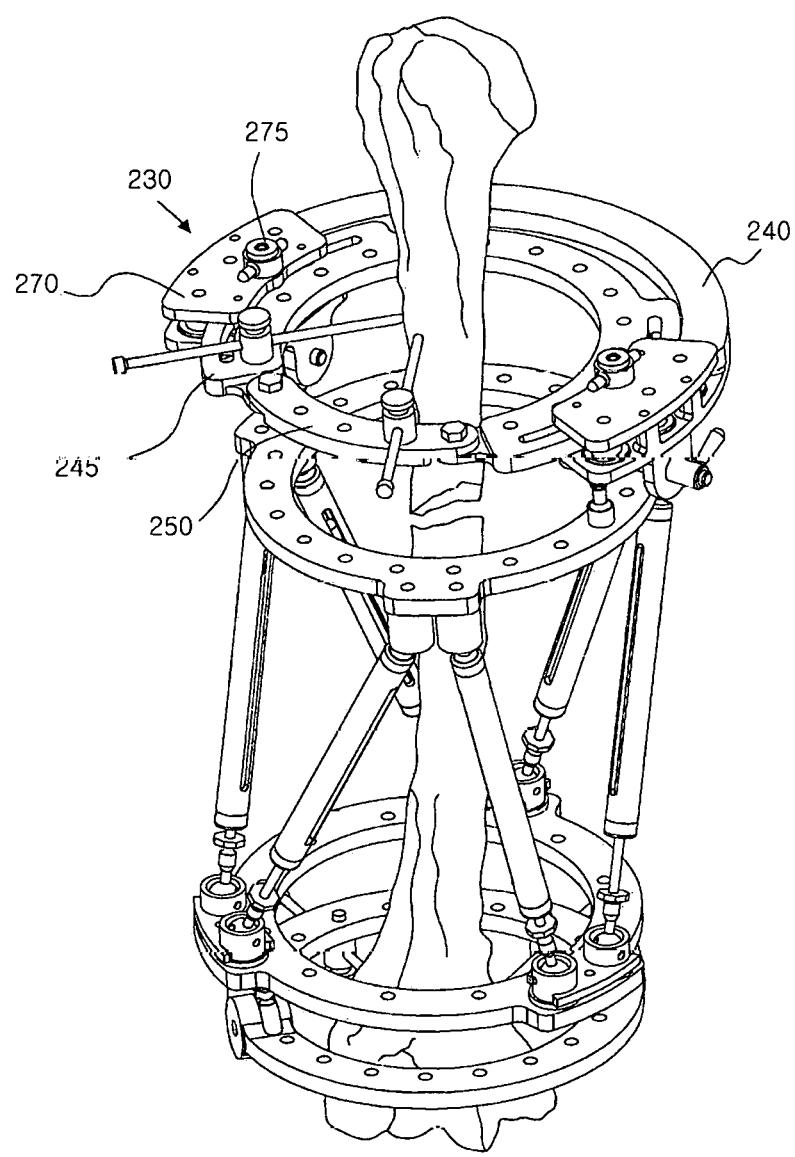
FIG. 10 is a perspective view showing an external fixator having a rotatable bone reduction frame according to still another embodiment of the present disclosure.
Figure 11:
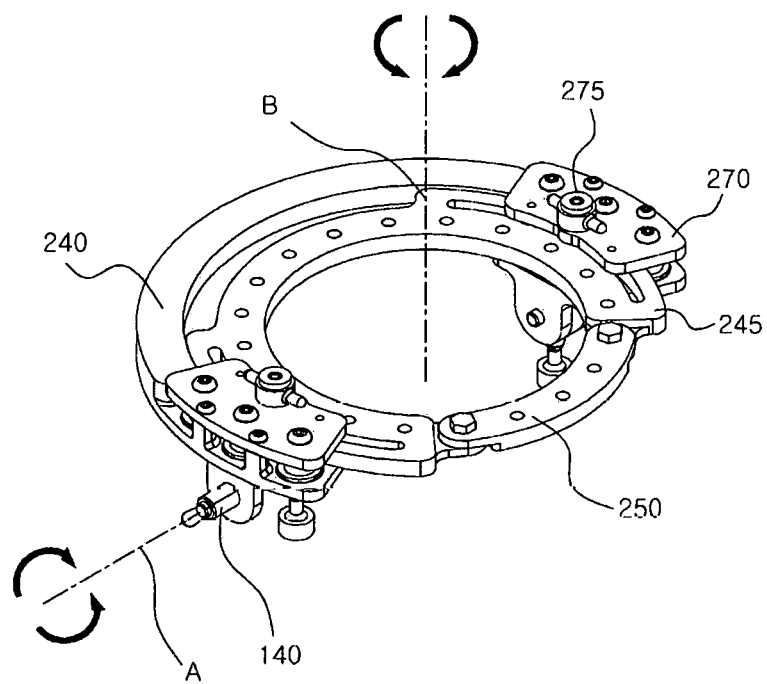
FIG. 11 is a diagram showing a rotatable bone reduction frame according to another embodiment of the present disclosure.
Figure 12:
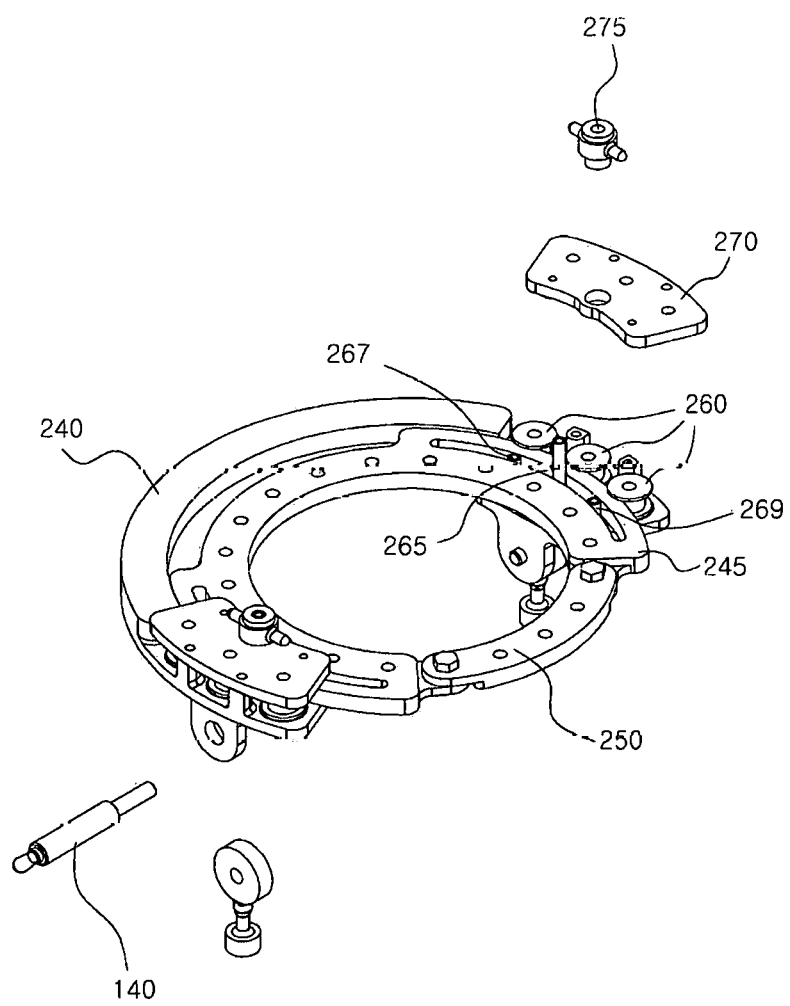
FIGS. 12 and 13 are exploded views showing the rotatable bone reduction frame according to another embodiment of the present disclosure.
Figure 13:
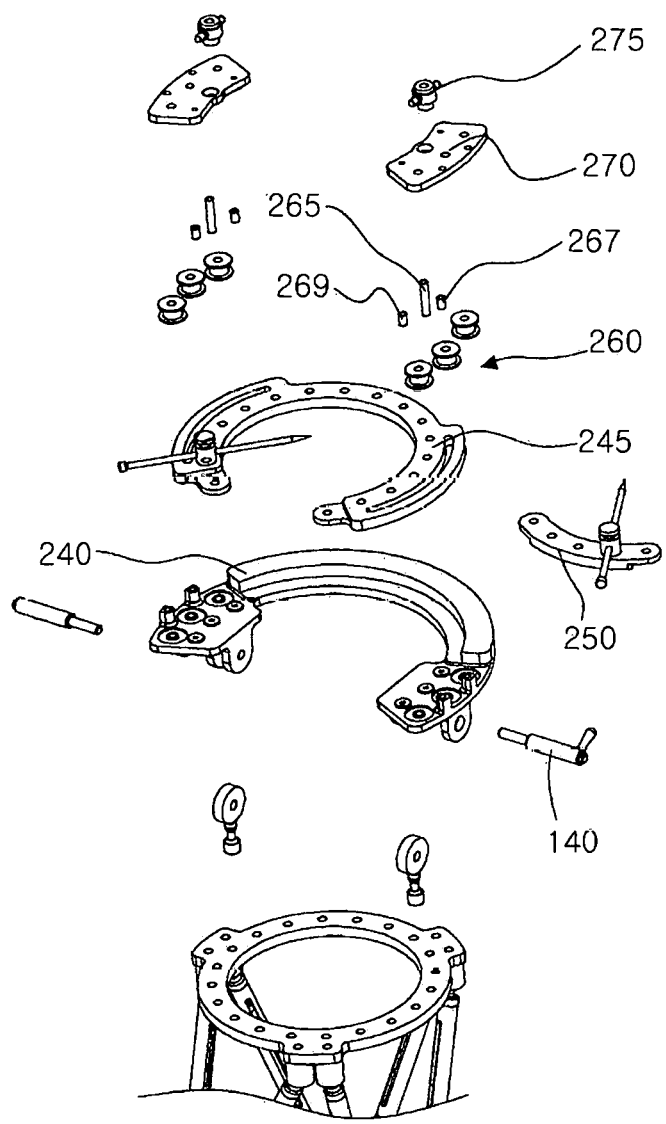
Figure 14A:
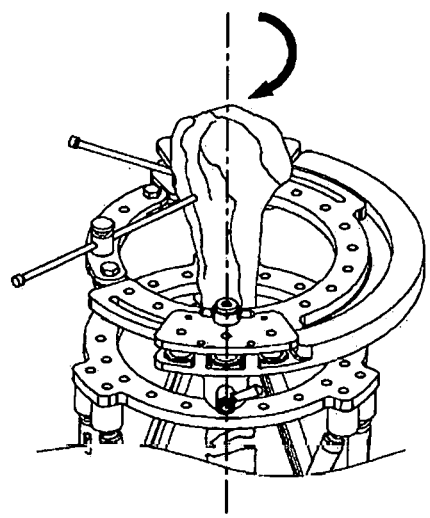
FIGS. 14A to 14C are diagrams for illustrating a rotating process of the rotatable bone reduction frame according to another embodiment of the present disclosure.
Figure 14B:
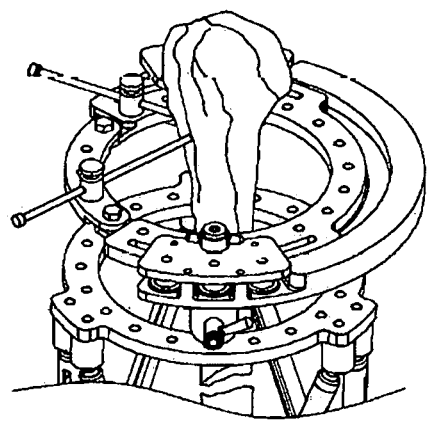
Figure 14C:
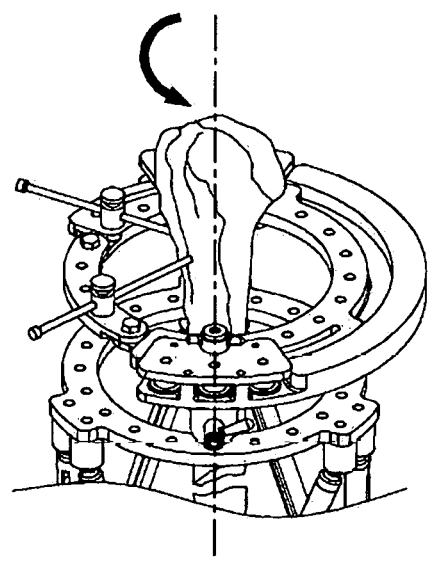

The external fixator having a rotatable bone reduction frame according to yet another embodiment of the present disclosure has been described. Hereinafter, an external fixator having a rotatable bone reduction frame according to still another embodiment of the present disclosure will be described with reference to FIGS. 10 to 14C. FIG. 10 is a perspective view showing an external fixator including a rotatable bone reduction frame according to still another embodiment of the present disclosure. FIG. 11 is a diagram showing the rotatable bone reduction frame according to still another embodiment of the present disclosure. FIGS. 12 and 13 are exploded views showing the rotatable bone reduction frame according to still another embodiment of the present disclosure. FIGS. 14A to 14C are diagrams for illustrating the rotating process of the rotatable bone reduction frame according to still another embodiment of the present disclosure.

Referring to FIGS. 10 to 14C, an external fixator 230 having a rotatable bone reduction frame according to still another embodiment of the present disclosure is not only rotatable based on a horizontal direction A as an axial direction but also rotatable based on a vertical direction B passing through the first frame 10 or the second frame 20 as an axial direction. The degree of rotation based on the horizontal direction A may be about 20° in a clockwise direction and a counterclockwise direction, respectively, and the degree of rotation based on the vertical direction B may be about 30° to the right and left, respectively. However, the degree of rotation may be adjusted as desired.

To this end, the first rotating frame installed on the first frame 10 among the rotating frames of the external fixator 230 includes a guide frame 240 with a space formed therein and forming a part of a circular shape, and a rotating body 245 located inside the guide frame 240, rotating along a curved surface of the guide frame 240 based on the vertical direction B as an axial direction and forming a part of a circular shape. At this time, a plurality of rollers 260 may be installed at both ends of the guide frame 240 to assist the rotating movement of the rotating body 245. The rollers 260 contact the periphery of the rotating body 245 and serve as a rotating guide. Also, only one roller may be installed, instead of the plurality of rollers 260.

In addition, two stop pins 267, 269 may be installed at both ends of the guide frame 240. The stop pins 267, 269 are positioned inside a perforation portion of the rotating body 245 with a slit shape that forms along the periphery of the rotating body 245. Thus, when the rotating body 245 rotates both ends of the penetration portion collide with the stop pins 267, 269 to limit the rotating range of the rotating body 245. Moreover, a mounting pin 265 may be installed between two stop pins 267, 269 on the guide frame 240. The mounting pin 265 may also protrude beyond the perforation portion of the rotating body 245. The mounting pin 265 may be located on the rotating body 245 and pass through the perforation hole of the cover 270, which may cover the roller 260.

In addition, a vertical fixing lever 275 located on the cover 270 and having a hollow into which the mounting pin 265 is inserted may be provided at the first rotating frame. The vertical fixing lever 275 presses the cover 270, and as a result, the rotating body 245 below the cover 270 is pressed to block rotation of the rotating body 245. As the rotation of the rotating body 245 is blocked by the vertical fixing lever 275, the degree of rotation of the rotating body 245 may be adjusted, thereby effectively performing the external fixation of the bone.

Moreover, seeing the rotating process of the first rotating frame with reference to FIGS. 14A to 14C, the first rotating frame may be rotated from an initial state (see FIG. 14B) to the left (see FIG. 14A) or to the right (see FIG. 14C). Also, in order to fix the first rotating frame at the rotated position, the rotating body 245 may be fixed by means of the vertical fixing lever 275 as described above.

In addition, an open portion is provided at the rotating body 245, and an opening frame 250 may be provided to open and close the open portion. The opening frame 250 may be detachably coupled to both ends of the rotating body 245 by using a coupling component such as a bolt and a nut. Since the opening frame 250 is provided to open the rotating body 245, the first rotating frame may be easily mounted on the bone subjected to bone reduction. In addition, a fixing member for anchoring a bone fragment with respect to the rotating body 245 or the opening frame 250 may be installed at the rotating body 245 or the opening frame 250. The fixing member may include a pin stuck into the bone fragment and a fixture for fixing the pin to the rotating body 245 or the opening frame 250.

As described above, since the external fixator 230 having a rotatable bone reduction frame according to still another embodiment of the present disclosure may rotate based on both the horizontal direction A and the vertical direction B as an axis, it is possible to effectively perform bone reduction to a fractured or deformed bone which has not been easily reduced in the existing technique.

Meanwhile, seeing the external fixing process of the external fixator having a rotatable bone reduction frame according to the present disclosure as described above, the rotating frame of the external fixator surrounds a fractured or deformed bone, and the bone is fixed using the fixing member installed at the rotating frame. After that, in a state where the horizontal and vertical fixing levers are released, the rotating frame is rotated based on the horizontal direction and the vertical direction as an axis to pull bone fragments. After pulling, the bone fragments are aligned to some extent, and then the rotating frame is fixed by means of the fixing levers. After that, the bone fragments are minutely corrected while varying the length of the variable leg.

In this way, by additionally installing the rotating frame at the first and second frames that constitute the upper and lower parts of an existing external fixator, the bone reduction area is enlarged in the vertical direction. In addition, since the rotating frame is rotatable based on the horizontal and vertical directions as an axis, the rotation degree of freedom of the external fixator is increased, and thus it is possible to effectively perform bone reduction to bone fractures, which is previously difficult to correct.

The external fixator including the rotating frame according to the present disclosure has been described. However, the rotating frame may be installed at the upper frame or the lower frame of the external fixator, or may be installed at both the upper frame and the lower frame. Also, the installed rotating frame may rotate based on the horizontal direction or the vertical direction as an axial direction or based on both in the horizontal direction and the vertical direction as an axis direction. In addition, the rotating frame may have a circular shape, a semicircular shape, or a partial circular shape between the circular shape and the semicircular shape.

The embodiments of the present disclosure have been described with reference to the accompanying drawings, but it will be understood by those skilled in the art that the present disclosure can be implemented in other specific forms without departing from the scope or essential characteristics thereof. Therefore, it should be understood that the embodiments described above are not restrictive but illustrative in all aspects.

The invention claimed is:

1. An external fixator for reduction of a fractured or deformed bone, comprising:
   a first frame having a configuration through which a bone passes;
   a second frame having a configuration through which the bone passes, the second frame being spaced apart from the first frame;
   a variable leg having both ends connected to the first frame and the second frame respectively and having a changeable length; and
   a rotating frame mounted to at least one of the first frame or the second frame to entirely or partially surround the bone, the rotating frame being rotatable with respect to an axial direction which is at least one direction of:
   a horizontal direction traversing the at least one of the first frame or the second frame, or
   a vertical direction perpendicular to the horizontal direction,
   wherein the rotating frame is rotatable with respect to the horizontal direction as the axial direction and includes a frame body, a support structure supporting the frame body with respect to the at least one of the first frame or the second frame, and a horizontal fixing lever blocking the rotation of the frame body.

2. The external fixator of claim 1, wherein the rotating frame includes:

a first rotating frame installed at the first frame, and
a second rotating frame installed at the second frame.

3. The external fixator of claim 1, wherein the support structure is accommodated into an insert space defined in the frame body, and
wherein the horizontal fixing lever is inserted into both of perforation holes of the frame body at both sides thereof and a perforation hole of the support structure, provides a friction between the frame body and the support structure, and blocks the rotation of the frame body.

4. The external fixator of claim 3, wherein the horizontal fixing lever includes a front length portion having a cylindrical shape and a rear length portion having a cylindrical shape and a larger diameter than the front length portion, and
wherein a protrusion defined at a point where the front length portion and the rear length portion meet provides the friction between the frame body and the support structure and blocks the rotation of the frame body.

5. The external fixator of claim 1, wherein the fixing structure fixing a bone fragment of the bone to the rotating frame is installed at the rotating frame, and the fixing structure includes a pin which is stuck into the bone fragment and a fixture for fixing the pin to the rotation frame.

6. The external fixator of claim 2, wherein the first rotating frame has a semicircular shape.

7. The external fixator of claim 1, wherein the rotating frame is rotatable with respect to the vertical direction as the axial direction, and wherein the rotating frame comprises:
a guide frame,
a rotating body located inside the guide frame and rotating along the inside of the guide frame, and
a vertical fixing lever blocking the rotation of the rotating body.

8. The external fixator of claim 7, further comprising:
a stop pin installed on the guide frame and located in a perforation hole defined at the rotating body to limit a rotating range of the rotating body, a cover located on the rotating body, and a mounting pin installed on the guide and located in the perforation hole of the rotating body to pass through a perforation hole of the cover,
wherein the vertical fixing lever is located on the cover and fit into the mounting pin to press the rotating body by the cover, and blocks the rotation of the rotating body.

9. The external fixator of claim 7, wherein the rotating body has a circular shape with an open portion, and an opening frame detachably coupled is located at both ends of the rotating body to open or close the open portion.

10. The external fixator of claim 9, wherein a fixing structure fixing a bone fragment of the bone to the rotating body or the opening frame is installed at the rotating body or the opening frame, and the fixing structure includes a pin stuck into the bone fragment and a fixture for fixing the pin to rotating body or the opening frame.

11. The external fixator of claim 1, wherein the variable leg is connected to the second frame by a ball joint and has a first leg and a second leg, each of the first leg and the second leg having a thread,
wherein the ball joint includes a ball connected to the first leg through a ball axle, the ball having a perforation hole passing through a center thereof, a ball housing located at the second frame, the ball housing having a fitting groove into which the ball is accommodated and a pair of insert holes defined at an outer surface of the ball housing along a direction traversing the fitting groove to face each other, and a pin member provided to extend over the pair of the insert holes to pass through the perforation hole, and
wherein as the ball housing rotates, the first leg rotates to fasten or release screw coupling between the first leg and the second leg and to change a length of the variable leg.

12. The external fixator of claim 1, wherein the length of the variable leg is changed by a detachable actuator.

13. The external fixator of claim 12, wherein the detachable actuator includes a surgical actuator and a portable actuator.

14. The external fixator of claim 12, wherein an operating time and operation details of the detachable actuator are controlled by a server.

15. An external fixator for reduction of a fractured or deformed bone, comprising:
a first frame having a configuration through which a bone passes;
a second frame having a configuration through which the bone passes, the second frame being spaced apart from the first frame;
a variable leg having both ends connected to the first frame and the second frame respectively and having a changeable length; and
a rotating frame mounted to at least one of the first frame or the second frame to entirely or partially surround the bone, the rotating frame being rotatable with respect to an axial direction which is at least one direction of:
a horizontal direction traversing the at least one of the first frame or the second frame, or
a vertical direction perpendicular to the horizontal direction,
wherein the rotating frame is rotatable with respect to the vertical direction as the axial direction, and wherein the rotating frame comprises:
a guide frame,
a rotating body located inside the guide frame and rotating along the inside of the guide frame, and
a vertical fixing lever blocking the rotation of the rotating body.

16. The external fixator of claim 15, further comprising:
a stop pin installed on the guide frame and located in a perforation hole defined at the rotating body to limit a rotating range of the rotating body, a cover located on the rotating body, and a mounting pin installed on the guide and located in the perforation hole of the rotating body to pass through a perforation hole of the cover;
wherein the vertical fixing lever is located on the cover and fit into the mounting pin to press the rotating body by the cover, and blocks the rotation of the rotating body.

17. The external fixator of claim 15, wherein the rotating body has a circular shape with an open portion, and an opening frame detachably coupled is located at both ends of the rotating body to open or close the open portion.

18. An external fixator for reduction of a fractured or deformed bone, comprising:
a first frame having a configuration through which a bone passes;
a second frame having a configuration through which the bone passes, the second frame being spaced apart from the first frame;
a variable leg having both ends connected to the first frame and the second frame respectively and having a changeable length; and
a rotating frame mounted to at least one of the first frame or the second frame to entirely or partially surround the bone, the rotating frame being rotatable with respect to an axial direction which is at least one direction of:

a horizontal direction traversing the at least one of the first frame or the second frame, or a vertical direction perpendicular to the horizontal direction, wherein when the rotating frame is rotatable with respect to the horizontal direction as the axial direction, the rotating frame includes a frame body rotatably coupled to at least one of the first frame or the second frame, and a horizontal fixing lever blocking the rotation of the frame body, and wherein when the rotating frame is rotatable with respect to the vertical direction as the axial direction, the rotating frame includes a rotating body rotatably coupled to at least one of the first frame or the second frame, and a vertical fixing lever blocking the rotation of the rotating body.

\* \* \* \* \*